United States Patent
Kucklick et al.

(10) Patent No.: US 8,821,387 B2
(45) Date of Patent: *Sep. 2, 2014

(54) ATRAUMATIC ARTHROSCOPIC INSTRUMENT SHEATH

(75) Inventors: Theodore R. Kucklick, San Jose, CA (US); Martin Trieb, Cloverdale, CA (US)

(73) Assignee: Cannuflow, Inc., San Jose, CA (US)

( * ) Notice: Subject to any disclaimer, the term of this patent is extended or adjusted under 35 U.S.C. 154(b) by 339 days.

This patent is subject to a terminal disclaimer.

(21) Appl. No.: 13/225,908

(22) Filed: Sep. 6, 2011

(65) Prior Publication Data

US 2012/0116164 A1    May 10, 2012

Related U.S. Application Data

(63) Continuation of application No. 12/251,351, filed on Oct. 14, 2008, now Pat. No. 8,012,083, which is a continuation of application No. 11/016,274, filed on Dec. 17, 2004, now Pat. No. 7,435,214, which is a continuation-in-part of application No. 10/769,629, filed on Jan. 29, 2004, now Pat. No. 7,413,542.

(51) Int. Cl.
*A61B 1/012* (2006.01)
*A61B 1/00* (2006.01)

(52) U.S. Cl.
USPC ........... 600/125; 600/121; 600/124; 600/114; 600/154; 604/539

(58) Field of Classification Search
USPC ......... 600/114, 128, 130, 153, 156, 115, 124, 600/125, 131, 154; 604/164.02, 264, 159, 604/160, 164.07, 165.01, 165.03, 533, 539
See application file for complete search history.

(56) References Cited

U.S. PATENT DOCUMENTS

| | | | |
|---|---|---|---|
| 4,646,722 A | | 3/1987 | Silverstein et al. |
| 4,717,379 A | | 1/1988 | Ekholmer |
| 4,721,097 A | * | 1/1988 | D'Amelio ..................... 600/123 |
| 4,765,314 A | | 8/1988 | Kolditz et al. |
| 4,820,265 A | | 4/1989 | DeSatnick et al. |
| 4,886,049 A | | 12/1989 | Darras |
| 4,897,079 A | * | 1/1990 | Zaleski et al. .................. 604/22 |
| 4,959,058 A | | 9/1990 | Michelson |
| 4,973,321 A | | 11/1990 | Michelson |

(Continued)

FOREIGN PATENT DOCUMENTS

| | | |
|---|---|---|
| JP | 1986217129 | 9/1986 |
| JP | U-1990-045703 | 1/1992 |

(Continued)

*Primary Examiner* — John P Leubecker
(74) *Attorney, Agent, or Firm* — K. David Crockett, Esq.; Susan L. Crockett, Esq.; Crockett & Crockett, PC

(57) ABSTRACT

A removable, resilient atraumatic sheath for arthroscopic instruments. The sheath covers sharp edges on the arthroscopic instrument, particularly the distal tip of the rigid cannula, and thereby protects tissue and objects near a surgical site from accidental trauma. The sheath may be provided in the form of an inflow/outflow sheath that allows a surgeon to irrigate and drain a surgical field without the use of a separate irrigation instrument. The sheath is provided with a cylindrical grip on the proximal end to resiliently squeeze the proximal end of the arthroscopic instrument. A lever is provided to move the grip radially outwardly to release the grip from the arthroscopic instrument.

12 Claims, 7 Drawing Sheets

(56) References Cited

U.S. PATENT DOCUMENTS

| | | | |
|---|---|---|---|
| 5,037,386 A | 8/1991 | Marcus et al. | |
| 5,156,142 A | 10/1992 | Anapliotis et al. | |
| 5,179,935 A | 1/1993 | Miyagi | |
| 5,273,545 A | 12/1993 | Hunt et al. | |
| 5,290,279 A | 3/1994 | Bonati et al. | |
| 5,413,092 A | 5/1995 | Williams, III et al. | |
| 5,449,356 A | 9/1995 | Walbrink et al. | |
| 5,458,606 A * | 10/1995 | Cohen et al. | 606/108 |
| 5,527,276 A | 6/1996 | Bruce | 604/506 |
| 5,575,756 A * | 11/1996 | Karasawa et al. | 600/157 |
| 5,593,394 A | 1/1997 | Kanesaka et al. | |
| 5,601,603 A | 2/1997 | Illi | |
| 5,637,075 A | 6/1997 | Kikawada | |
| 5,643,174 A * | 7/1997 | Yamamoto et al. | 600/114 |
| 5,762,604 A | 6/1998 | Kieturakis | |
| 5,797,882 A | 8/1998 | Purdy et al. | |
| 5,797,943 A | 8/1998 | Danks et al. | |
| 5,924,977 A | 7/1999 | Yabe et al. | |
| 5,941,815 A * | 8/1999 | Chang | 600/114 |
| 5,989,183 A * | 11/1999 | Reisdorf et al. | 600/156 |
| 6,110,103 A * | 8/2000 | Donofrio | 600/121 |
| 6,117,068 A * | 9/2000 | Gourley et al. | 600/35 |
| 6,120,434 A * | 9/2000 | Kimura et al. | 600/114 |
| 6,159,160 A | 12/2000 | Hsei et al. | |
| 6,203,537 B1 | 3/2001 | Adrian | |
| 6,269,340 B1 | 7/2001 | Ford et al. | |
| 6,293,909 B1 | 9/2001 | Chu et al. | |
| 6,447,446 B1 * | 9/2002 | Smith et al. | 600/157 |
| 6,558,379 B1 | 5/2003 | Batchelor et al. | |
| 6,585,639 B1 | 7/2003 | Kotmel et al. | |
| 6,692,431 B2 | 2/2004 | Kazakevich | |
| 6,827,710 B1 | 12/2004 | Mooney et al. | |
| 6,878,149 B2 | 4/2005 | Gatto | |
| 8,012,083 B2 * | 9/2011 | Kucklick et al. | 600/114 |
| 2001/0056222 A1 | 12/2001 | Rudischhauser et al. | |
| 2003/0004400 A1 | 1/2003 | Smith | |
| 2003/0018340 A1 | 1/2003 | Branch | |
| 2004/0082915 A1 | 4/2004 | Kadan | |
| 2005/0025438 A1 | 2/2005 | Go et al. | |
| 2005/0085695 A1 | 4/2005 | Shener et al. | |
| 2005/0209506 A1 * | 9/2005 | Butler et al. | 600/114 |
| 2005/0267331 A1 * | 12/2005 | Secrest et al. | 600/114 |
| 2006/0041186 A1 | 2/2006 | Vancaillie | |

FOREIGN PATENT DOCUMENTS

| | | |
|---|---|---|
| JP | 1994038902 | 5/1994 |
| JP | 1998092601 | 6/1998 |
| WO | WO2005072402 | 8/2005 |

\* cited by examiner

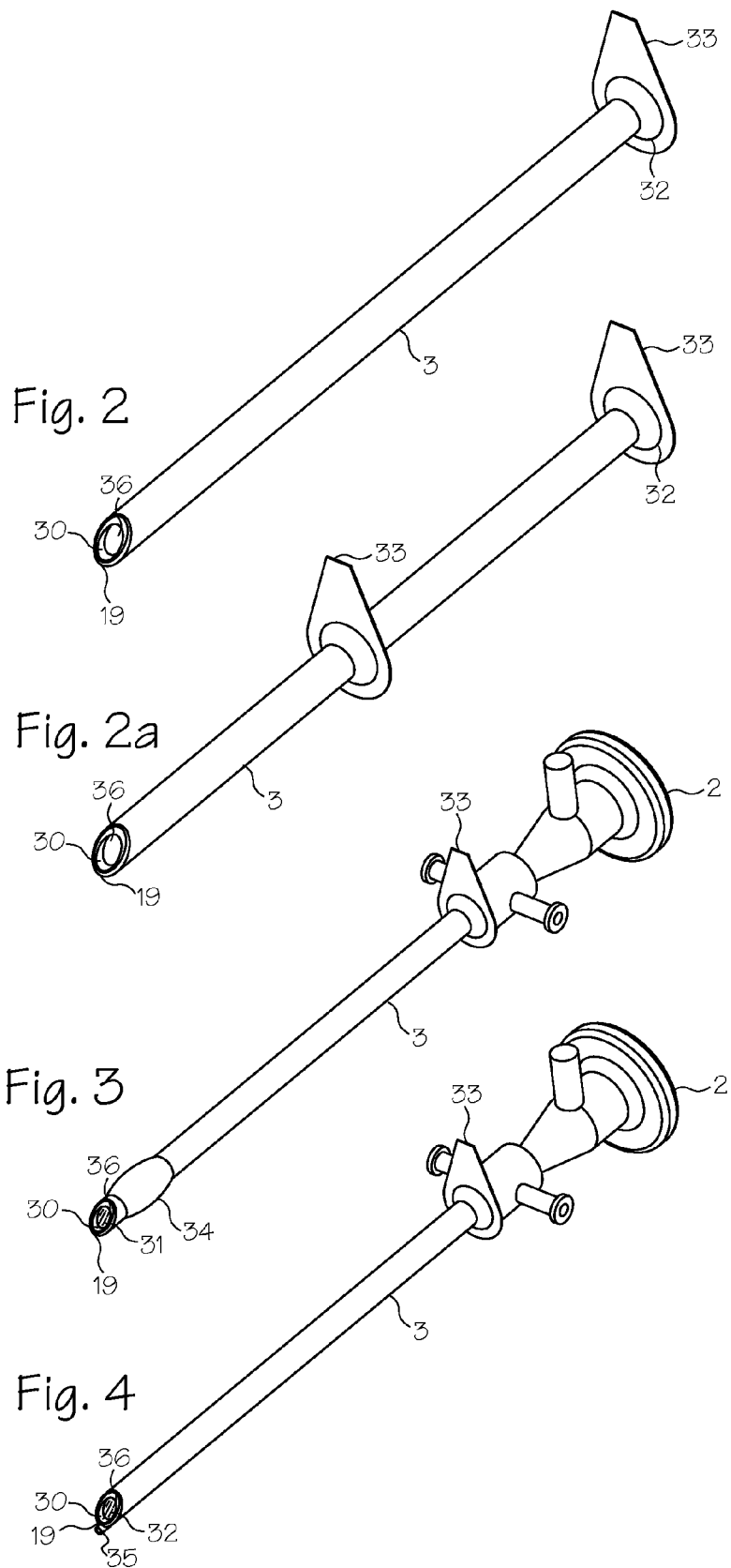

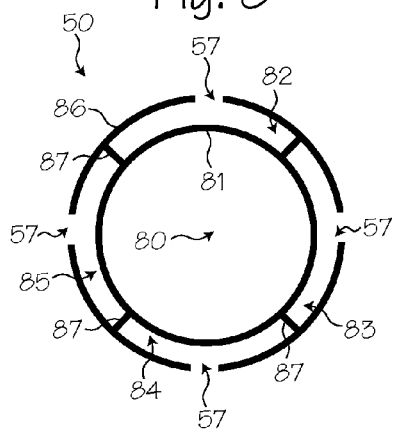
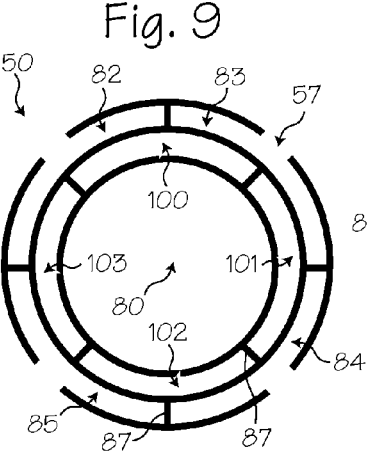
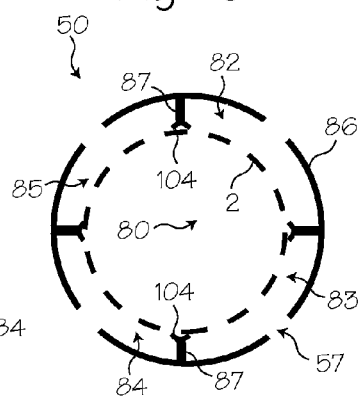
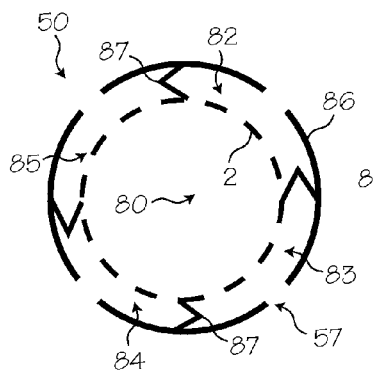
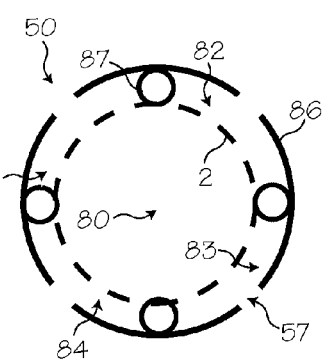
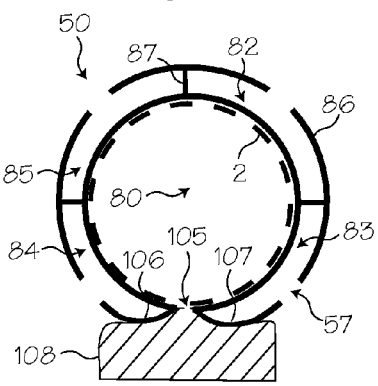
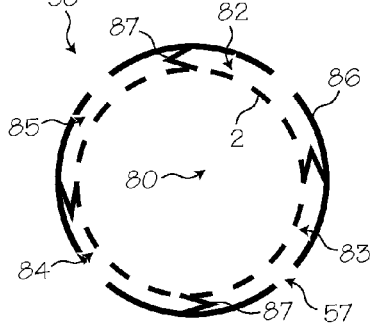
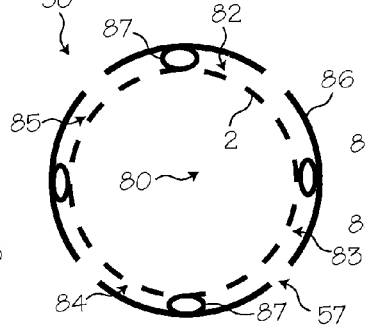
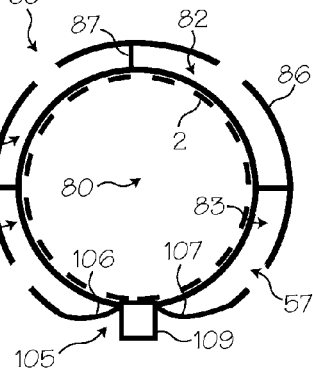

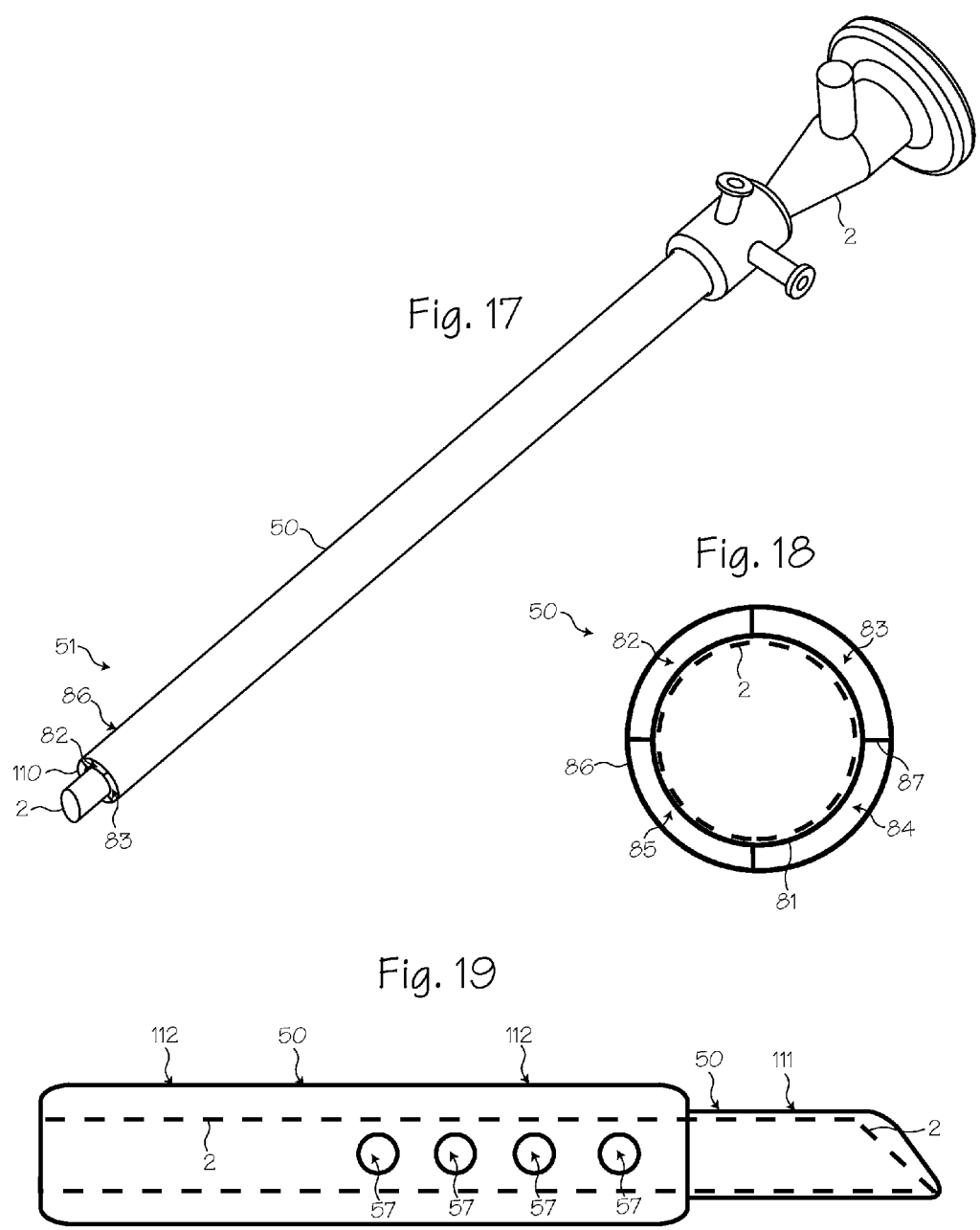

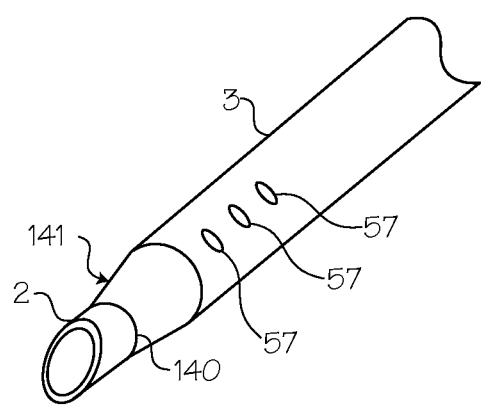
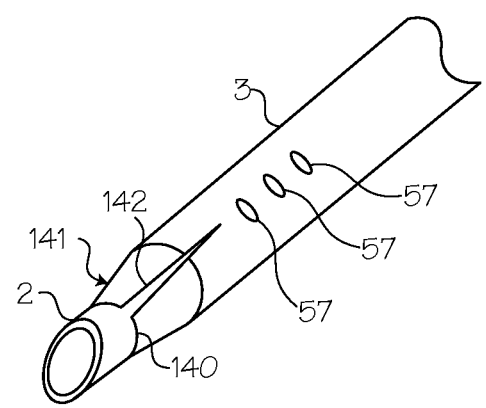

ATRAUMATIC ARTHROSCOPIC INSTRUMENT SHEATH

This application is a continuation of U.S. patent application Ser. No. 12/251,351, filed Oct. 14, 2008, now U.S. Pat. No. 8,012,083, which is a continuation of U.S. patent application Ser. No. 11/016,274, filed Dec. 17, 2004, now U.S. Pat. No. 7,435,214, which in turn is a continuation-in-part of U.S. patent application Ser. No. 10/769,629, filed Jan. 29, 2004, now U.S. Pat. No. 7,413,542.

FIELD OF THE INVENTIONS

The inventions described below relate the field of arthroscopic surgical instruments.

BACKGROUND OF THE INVENTIONS

Arthroscopic surgery involves using optical instruments, such as an arthroscope, to visualize an operating field inside or near a joint of a patient. The same instrument or other instruments may be used to perform a surgical procedure in the operating field. Common instruments used in addition to the arthroscope include a trimming instrument for cutting tissue and an irrigation instrument for irrigating the surgical field. Each of the instruments requires its own incision to be introduced into the surgical field; thus, many surgeons prefer to use only a trimming instrument and an arthroscope during arthroscopic surgical procedures.

Arthroscopes are fragile in relation to the forces applied during arthroscopic surgery, so a rigid cannula is placed over the arthroscope to reinforce it. The distal end of the rigid cannula is pointed, usually sharp, and so the rigid cannula can scratch or gouge soft tissue within the operating field. The rigid cannula can also become stuck between bones or cartilage during a procedure. A rigid cannula can also damage metal prosthetics used to replace joints, resulting in a shortening of the useful life of the prosthetic and forcing the patient to undergo additional, painful surgeries to correct the problem.

An additional problem associated with arthroscopic surgery is maintaining a clear surgical field during surgery. Blood and debris can cloud the field, impairing a surgeon's ability to visualize tissue. One method of solving this problem is to use the irrigation instrument to clear the surgical field with saline; however, many surgeons strongly prefer to avoid the additional trauma caused by inserting a third instrument. These surgeons will perform arthroscopic surgeries despite problems with visualizing the surgical field. Thus, devices and methods are needed both to maintain a clear surgical field and reduce accidental injury to the patient while only using two instruments.

SUMMARY

The devices and methods shown below provide for a soft plastic, disposable atraumatic sheath that slides over the rigid cannula of an arthroscope. The distal end of the atraumatic sheath extends slightly past the distal end of the rigid cannula, thereby providing a soft, blunt cushion over the distal end of the rigid cannula. The atraumatic sheath thereby protects any surrounding tissue or objects from accidental injury or damage while the arthroscope is manipulated inside the operating field.

The atraumatic sheath may also be provided as an inflow/outflow sheath that allows a surgeon to drain fluids from or introduce fluids into the surgical field, thereby keeping the surgical field clear. The inflow/outflow sheath is a multilumen tube into which the arthroscope is inserted. The proximal portion of the sheath is provided with fluid ports, a manifold and other means of controlling the flow of fluid inside the sheath. The distal portion of the inflow/outflow sheath is provided with a plurality of holes. Each hole communicates with one or more of the lumens inside the tube, thereby allowing fluid to flow between the surgical field and sources or sinks located outside the patient. The inflow/outflow sheath thereby allows the surgeon to maintain a clear surgical field and protect the patient from accidental injury while eliminating the need for a third irrigation instrument.

BRIEF DESCRIPTION OF THE DRAWINGS

FIG. 2 shows an atraumatic sheath for use with arthroscopic instruments.

FIG. 2a shows an atraumatic sheath having two tabs.

FIG. 3 shows an atraumatic sheath for use with arthroscopic instruments and an arthroscope disposed inside the atraumatic sheath.

FIG. 4 shows an atraumatic sheath for use with arthroscopic instruments, an arthroscope disposed inside the atraumatic sheath and an irrigation tube disposed on the sheath.

FIG. 8 shows a cross section of the distal portion of the inflow/outflow atraumatic sheath of FIG. 7.

FIG. 9 shows a cross section of the distal portion of an inflow/outflow atraumatic sheath.

FIG. 10 shows a cross section of the distal portion of an inflow/outflow atraumatic sheath.

FIG. 11 shows a cross section of the distal portion of an inflow/outflow atraumatic sheath.

FIG. 12 shows a cross section of the distal portion of an inflow/outflow atraumatic sheath.

FIG. 13 shows a cross section of the distal portion of an inflow/outflow atraumatic sheath.

FIG. 14 shows a cross section of the distal portion of an inflow/outflow atraumatic sheath.

FIG. 15 shows a cross section of the distal portion of an inflow/outflow atraumatic sheath.

FIG. 16 shows a cross section of the distal portion of an inflow/outflow atraumatic sheath.

FIG. 17 shows an inflow/outflow atraumatic sheath for use with arthroscopic instruments.

FIG. 18 shows a cross section of the distal portion of the inflow/outflow sheath shown in FIG. 17.

FIG. 19 shows an inflow/outflow sheath having a distal portion that has an inner diameter that closely conforms to the outer diameter of the distal portion of an arthroscope.

FIG. 25 shows the distal portion of an atraumatic sheath and an arthroscope extending distally of the distal end of the sheath.

FIG. 26 shows the distal portion of an atraumatic sheath and an arthroscope extending distally of the distal end of the sheath.

DETAILED DESCRIPTION OF THE INVENTIONS

Figure 1:
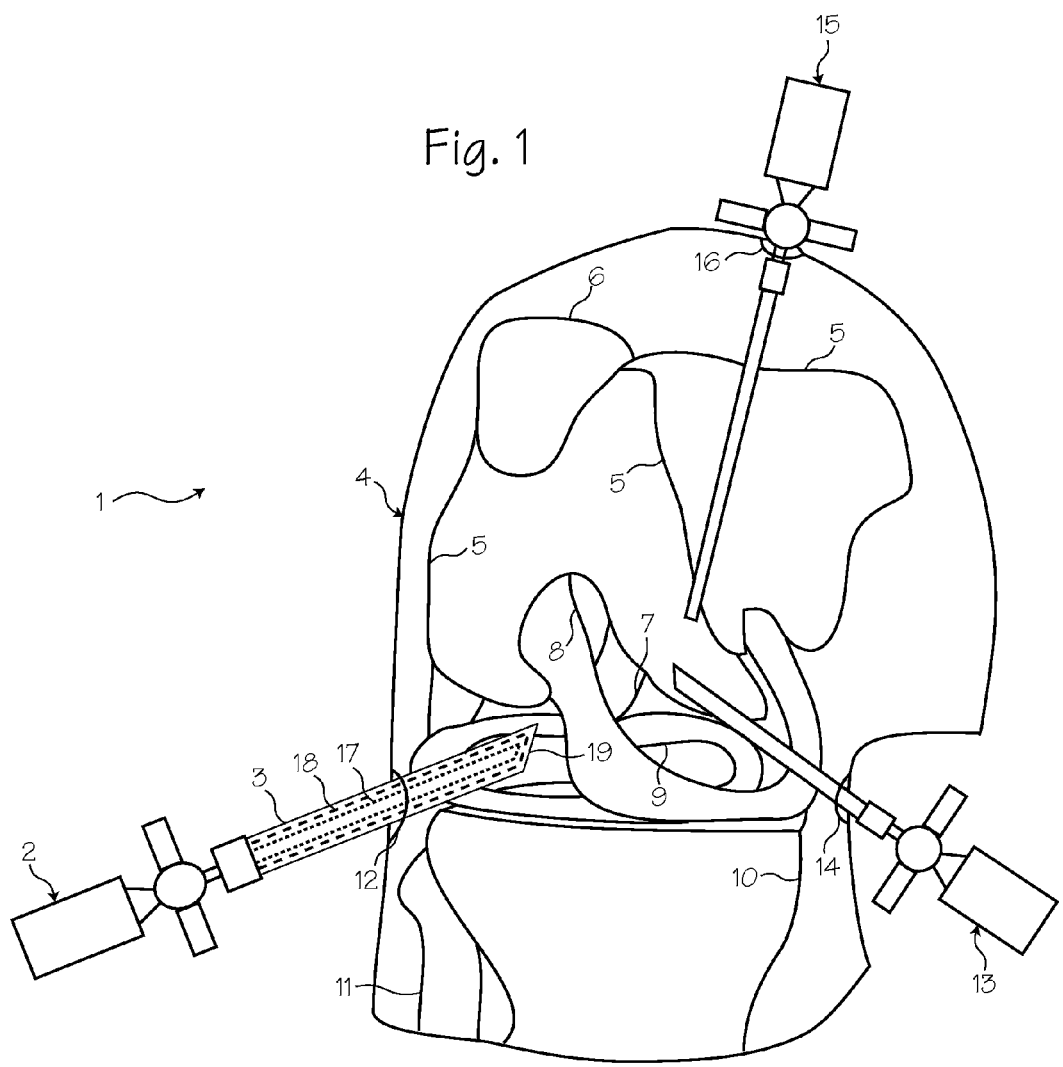
FIG. 1 shows a method of performing arthroscopic surgery on a patient.

FIG. 1 shows a method of performing arthroscopic surgery on a patient by using an arthroscopic instrument 2 sheathed in an atraumatic introducer sheath 3. An arthroscopic instrument may be an arthroscope, endoscope, awl, pick, shaver, etc. In FIG. 1, the arthroscopic instrument 2 shown is an arthroscope. (The various parts of the arthroscope are shown in phantom to indicate their positions inside the sheath.) Various anatomical landmarks in the patient's knee 4 are shown for reference, including the femur 5, patella 6, posterior cruciate ligament 7, anterior cruciate ligament 8, meniscus 9, tibia 10 and fibula 11. During surgery, the surgeon introduces the arthroscope 2 into the knee via a first incision 12 in order to visualize the surgical field. A trimming instrument 13 is introduced through a second incision 14 to remove or trim tissue that the surgeon determines should be removed or trimmed. Optionally, an irrigating instrument 15 may be introduced through a third incision 16 in order to irrigate the surgical field and thereby maintain a clear view. As provided below, the irrigating instrument may be replaced by a combined arthroscope and inflow/outflow atraumatic sheath, thus reducing the number on incisions required to perform the surgery.

The arthroscope 2 is an optical instrument 17 surrounded by a rigid cannula 18 having a distal edge that typically is cut at an angle. To protect the patient from unintended injury or trauma during the procedure, the arthroscope has been inserted into a resilient, outer introducer sheath or atraumatic sheath 3 that extends over the rigid cannula. The distal tip 19 of the atraumatic sheath extends distally just past the distal end of the arthroscope and rigid cannula to further protect the patient.

FIGS. 2 through 4 illustrate the atraumatic sheath 3. The atraumatic sheath is a tube of a resilient material, such as a soft plastic or rubber. The inner diameter of the atraumatic sheath is sized and dimensioned to closely fit over the outer diameter of an arthroscopic instrument. The distal tip 19 of the atraumatic sheath is provided with a shape that closely approximates the shape of the distal tip of the arthroscope and/or the rigid cannula. A flange 30 disposed around the distal end of the sheath prevents the distal tip of the rigid cannula from gouging the patient. The flange is integral with the walls of the sheath and extends inwardly towards the axis of the sheath. The flange is sized and dimensioned to prevent the distal tip of the rigid cannula from accidentally slipping distally during a surgical procedure. An opening 36 is provided in some atraumatic sheaths so that the surgeon may insert the endoscope or other instruments through the opening and into the surgical space. The distal lens 31 of an optical instrument is shown for reference in FIGS. 3 and 4.

Figure 7:
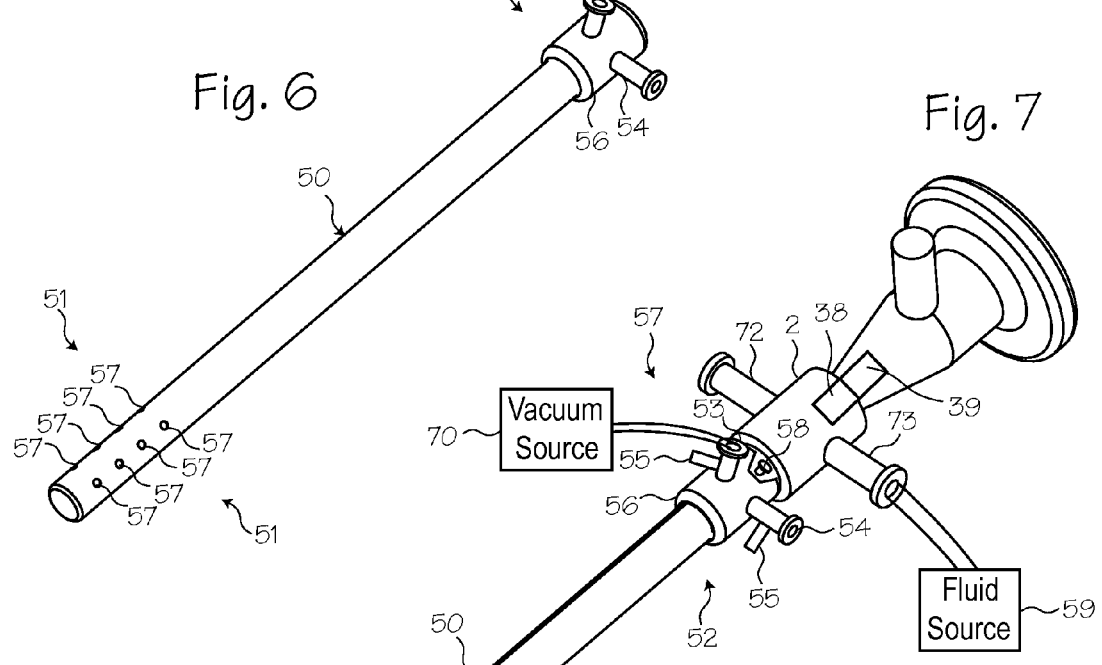
FIG. 7 shows an inflow/outflow atraumatic sheath for use with arthroscopic instruments and an arthroscope disposed inside the atraumatic sheath.

The proximal end 32 of the atraumatic sheath is provided with a tab 33 to allow medical personnel to easily pull the atraumatic sheath over the rigid cannula, arthroscope and/or arthroscopic instrument. The proximal end of the atraumatic sheath may also be provided with fittings 38, such as a locking hub or snap latches, that attach to fittings 39 or openings disposed on the arthroscope or other instrument, thereby securing the atraumatic sheath as illustrated in FIG. 7.

The tab 33 is sized and dimensioned to divert liquids away from any device proximal the atraumatic sheath, such as cameras, optics, motors and other equipment that may be sensitive to liquids or moisture. Liquids that escapes the surgical site and that travel along the outer surface of the sheath will be deflected by the tab, which has a radial dimension greater than that of the lumen of the sheath.

FIG. 2a shows an atraumatic sheath 3 having two tabs 33 disposed along the longitudinal length of the sheath. If the flow of liquids is expected to be heavy for a surgical procedure, then the additional tab ensure that liquids do not reach sensitive devices located proximally of the sheath. Additional tabs may be provided along the longitudinal length of the sheath.

Figure 5:
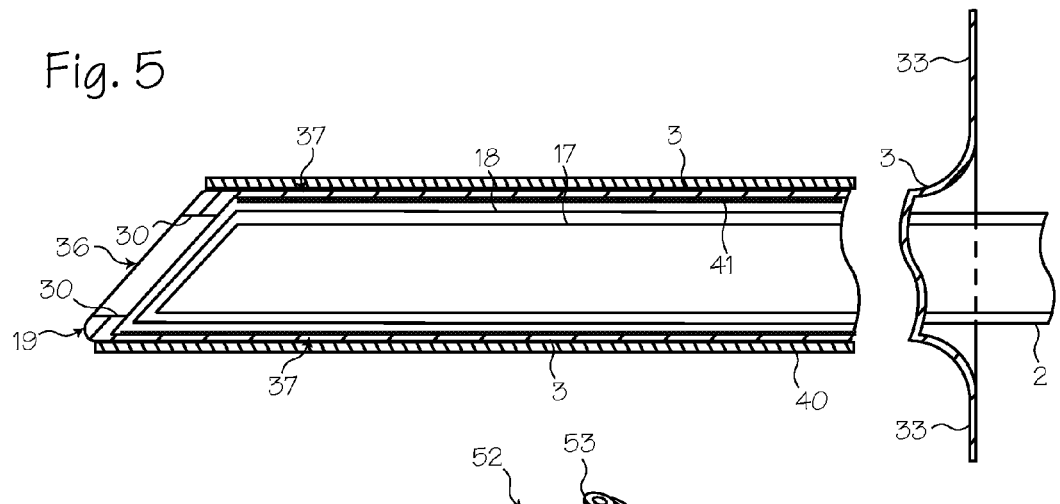
FIG. 5 shows a cross section of the atraumatic sheath shown in FIG. 2 and an arthroscopic instrument disposed inside the atraumatic sheath.

The outer surface of the atraumatic sheath may be provided with a smooth coating 40 as shown in FIG. 5 to allow the arthroscope and rigid cannula to more easily move within an operating site. For example, the sheath may be provided with a Teflon® (PTFE or expanded polytetrafluoroethylene) coating or covered with a water-activated lubricant. In contrast, the inner surface of the atraumatic sheath (the walls that define the lumen of the tube) may be provided with a non-slip coating 41 or other high coefficient of friction coating. For example, the inner surface of the atraumatic sheath may be coated with a co-extruded tacky thermoplastic elastomer (TPE). The non-slip coating prevents the sheath from easily slipping over the outer surface of the rigid cannula or arthroscope, thereby helping to prevent the atraumatic sheath from twisting or slipping around the arthroscope.

FIGS. 3 and 4 show an atraumatic sheath 3 for use with arthroscopic instruments and an endoscope or arthroscope 2 disposed inside the atraumatic sheath. The atraumatic sheath shown in FIG. 3 is provided with a balloon 34 on the distal portion of the sheath. (The balloon may be integrally formed with the sheath.) The balloon allows a surgeon to open a space within tissue, thereby dissecting the surgical field. The arthroscope may then be extended distally out of the opening 36 and the surgical space visualized. In addition, the distal end of the sheath may be provided with a distally projecting spoon or other distally projecting object to prop open a space in front of the arthroscope. The balloon and the distally projecting spoon thus provide a means for dissecting or retracting tissue to form a small surgical space.

FIG. 4 shows an atraumatic sheath 3 having a second, working tube 35. The working tube allows irrigation, fiber optics, sutures, needles, probes or surgical tools through the lumen. The atraumatic sheath shown in FIG. 4 may be combined with the atraumatic sheath shown in FIG. 3 to provide an atraumatic sheath with both a balloon and a working tube.

FIG. 5 shows a cross section of the atraumatic sheath 3 shown in FIG. 2 and an arthroscopic instrument 2 disposed inside the sheath. The atraumatic sheath is provided with a tab 33 on the proximal end of the sheath in order to increase the ease of pulling the sheath over the arthroscope. The distal end of the sheath is provided with an opening 36 to allow light to pass between the arthroscope and the operating space and, optionally, to allow additional instruments to pass through or alongside the arthroscope and into the surgical field. The walls 37 of the sheath at the distal end 19 of the sheath are thicker than the rest of the sheath walls to form a flange 30 at the distal end of the sheath. (The flange may be a separate ring of material attached to the inside of the sheath.) The flange covers the sharp distal tip of the arthroscopic instrument and prevents the instrument from slipping distally through opening 36. The rest of the walls of the atraumatic sheath are thin in order to minimize the overall thickness of the combined sheath and arthroscopic instrument.

In use, the atraumatic sheath is provided and pulled over an arthroscopic instrument. (The instrument may also be thought of as being inserted into the sheath.) The sheathed arthroscopic instrument is then inserted into the surgical site and the surgeon performs a medical procedure therein. If a balloon is provided, the balloon is used to dissect tissue so that the arthroscope may be extended distally out of the opening 36 and the surgical space visualized.

Figure 6:
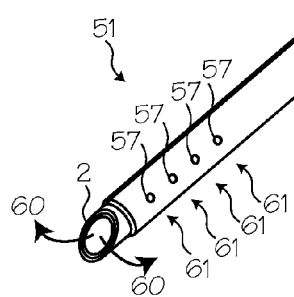
FIG. 6 shows an inflow/outflow atraumatic sheath for use with arthroscopic instruments.

FIGS. 6 and 7 show an inflow/outflow atraumatic sheath 50 and an arthroscope 2 disposed inside the sheath. Like the sheath shown in FIG. 2, the inflow/outflow atraumatic sheath 50 is formed of a resilient material that protects the patient from accidental injury should the arthroscope poke at or scrape along tissue. The sheath material may also be radiopaque. A preferred durometer hardness of the sheath material is in the range of about 40 Shore D to about 90 Shore D. In this hardness range the sheath is sufficiently resilient that the sheath protects the patient from accidental injury but is sufficiently hard to prevent the lumens within sheath from collapsing.

The inflow/outflow sheath 50 is a multi-lumen tube into which an arthroscope is inserted. Each lumen extends from the distal portion 51 of the sheath to the proximal portion 52 of the sheath. The proximal portion of the sheath is provided with one or more fluid ports, such as first port 53 or second port 54; one or more stopcocks 55 or fluid switches; one or more valves, such as a check valve; a manifold 56; or other means of controlling the flow of fluid inside the sheath. The distal portion 51 of the inflow/outflow sheath is provided with a plurality of holes 57. Each hole communicates with one or more of the lumens inside the tube, thereby allowing fluid to flow between the surgical field and the lumens inside the sheath.

Prior to surgery, medical personnel or the device manufacturer inserts the arthroscope into the inflow/outflow atraumatic sheath and secures the sheath to the arthroscope via a set-screw, snap-on attachment, other releasable attachments or other means 58 for securing the sheath to the arthroscope. During use, a surgeon may cause a fluid, preferably saline, to flow from a fluid source 59, through the arthroscope and into the surgical field, as shown by inflow arrows 60. (The arthroscope is provided with one or more lumens, ports or working tubes that allow fluid to flow through the arthroscope and into the surgical field.) In turn, blood, other fluids and debris are drained from the surgical field through the holes 57, as shown by outflow arrows 61, and flow through one or more lumens in the sheath. The inflow of clear saline and the outflow of cloudy fluid and debris allow the surgeon to maintain a clear surgical field using a single instrument. In turn, this capability eliminates the need to use an irrigating instrument. Thus, the surgeon may have a clear field of view while using only a two-incision arthroscopic procedure.

FIG. 7 also shows that fluids are drained through the inflow/outflow atraumatic sheath by using a vacuum source 70 or gravity drain operatively attached to a fluid port, such as port 53, connected to the sheath manifold 56. Fluids are provided through the arthroscope 2 from a fluid source 59 (by using a pump or gravity feed) operatively attached to a fluid port, such as third port 72 or fourth port 73 connected to the arthroscope. Depending on the capabilities of the arthroscope and the surgeon's needs, the vacuum source and fluid source may be connected to different combinations of ports provided with the inflow/outflow sheath or the arthroscope. For example, the vacuum source may be attached to port 73 and the fluid source may be attached to port 72 on the inflow/outflow sheath. In this case, the surgeon may both introduce fluids into and drain fluids from the surgical site using only the inflow/outflow sheath. Thus, even if the arthroscope is incapable of introducing fluids to or draining fluids from the surgical site, the inflow/outflow sheath allows the surgeon to eliminate the need for the irrigation instrument. In any case, a pressure sensor, and flow rate control system and feedback control system may be provided to automatically monitor and control the rate of fluid flow into and out of the surgical site.

FIG. 8 shows a cross section of the distal portion of the inflow/outflow sheath 3 shown in FIG. 6. The inflow/outflow sheath 50 has a central lumen 80, bounded by inner wall 81, through which the arthroscope is inserted. The sheath has four outer lumens, including a first outer lumen 82, a second outer lumen 83, a third outer lumen 84 and a fourth outer lumen 85 bounded by the inner wall 81, the outer wall 86 and four relatively stiff ribs 87 that extend between the inner and outer walls and that run along the length of the sheath. The outer lumens are annular. The distal end of the sheath in the area of the outer lumens 82, 83, 84 and 85 is sealed closed and provided with a rounded shape to help prevent injury to the patient (the central lumen remains open to accommodate the arthroscopic instrument). Holes 57 or apertures disposed in the outer wall allow fluids to flow into or out of the outer lumens. For example, lumens 82 and 84 could serve as passages through which fluids are introduced into the surgical site and lumens 83 and 85 could serve as passages through which fluids are drained from the surgical site. During another surgical procedure, all four lumens could be used to either drain or introduce fluids. Thus, the surgeon has the option of using the inflow/outflow atraumatic sheath in many different modes. (In addition, the sheath may be formed with more than or fewer than the four ribs shown, so long as at least one outer lumen remains open to fluid flow after the sheath and scope have been inserted into the surgical site.)

FIGS. 9 through 16 show cross sections of the distal portion of various inflow/outflow atraumatic sheaths. FIG. 9 shows an inflow/outflow sheath having a second set of inner lumens, including a first inner lumen 100, a second inner lumen 101, a third inner lumen 102 and a fourth inner lumen 103. With this design, the surgeon can increase the rate of fluid exchange by using all of the inner lumens to introduce fluids into the surgical site and by using all of the outer lumens 82, 83, 84 and 85 to drain fluid from the surgical site (or visa versa).

FIG. 10 shows an inflow/outflow sheath 50 without an inner wall. Instead, the outer surface of the arthroscope 2 serves as the inner wall of the sheath once the arthroscope has been inserted into the sheath. The four, relatively stiff ribs 87 form a seal with the outer surface of the arthroscope, thereby creating the four outer lumens 82, 83, 84 and 85. The ends of the ribs may be provided with elastic flanges 104 to enhance the seal made between the ribs and the arthroscope. This configuration reduces the overall size of the combined inflow/outflow sheath and arthroscope. (If the outer wall 86 is made of an elastomeric material, then the tube can stretch radially to accommodate a variety of sizes of arthroscopes.)

FIG. 11 shows an inflow/outflow atraumatic sheath 50 similar to that shown in FIG. 10. The relatively hard ribs 87 are pleated, but still form a seal with the outer wall of the arthroscope 2, thereby forming the outer lumens 82, 83, 84 and 85 once the arthroscope is inserted into the sheath. The sheath of FIG. 11 accommodates a variety of sizes of arthroscopes since the pleated ribs will bend to a degree necessary to accommodate larger sizes of arthroscopes, as shown in FIG. 12.

FIG. 13 shows an inflow/outflow atraumatic sheath 50 similar to that shown in FIG. 11. The ribs 87 of this sheath are elastic tubes that form a seal with the outer wall of the arthroscope 2, thereby forming the outer lumens 82, 83, 84 and 85 once the arthroscope is inserted into the sheath. The sheath of FIG. 13 accommodates a variety of sizes of arthroscopes since the tubes will compress to a degree necessary to accommodate larger sizes of arthroscopes, as shown in FIG. 14.

FIG. 15 shows a "C"-shaped or slit inflow/outflow sheath 50. Like the sheath of FIG. 8, four outer lumens 82, 83, 84 and 85 are provided, with the outer lumens bounded by three ribs 87, the inner wall 81 and the outer wall 86. When the arthroscope 2 is inserted into the sheath, a small gap 105 may form between the respective tips of the first arcuate segment 106 and the second arcuate segment 107. (As the arthroscope is inserted into the surgical space, tissue 108 will seal the gap and prevent fluids from leaking from the surgical space to outside the body.) The sheath of FIG. 15 accommodates a variety of sizes of arthroscopes since the arcuate segments will move radially outwardly as a larger arthroscope is inserted into the sheath, as shown in FIG. 16.

Optionally, a protrusion or a guide rail 109 may extend from either the arthroscope or the sheath. The guide rail helps the user align the sheath on the arthroscope while inserting the arthroscope into the sheath. The guide rail also prevents unwanted rotation or twisting of the sheath over the arthroscope during a surgical procedure.

FIGS. 17 and 18 show an inflow/outflow atraumatic sheath 50 and an arthroscope 2 inserted into the sheath. In contrast to the inflow/outflow sheaths shown in FIGS. 6 through 16, the outer wall 86 of the distal portion 51 of the sheath is made from a continuous tube (the distal portion of the sheath is not provided with holes). Nevertheless, like the sheath of FIG. 8 the sheath of FIG. 17 has an inner lumen to accommodate the arthroscope and four outer lumens to accommodate fluid inflow and outflow, including a first outer lumen 82, a second outer lumen 83, a third outer lumen 84, and a fourth outer lumen 85. The outer lumens are bounded by the inner wall 81, outer wall 86 and supporting ribs 87. The instrument shown in FIG. 17 provides fluid inflow and outflow out of the distal end 110 of the sheath.

FIG. 19 shows an inflow/outflow atraumatic sheath 50 having a closely-conforming distal portion 111 that has an inner diameter that closely conforms to the outer diameter of the distal portion of an arthroscope 2. The fluid-conducting portion 112 of the sheath is set proximally from the closely conforming distal portion 111 of the sheath. The outer diameter of the fluid conducting portion 112 and the outer diameter of the closely conforming distal portion 111 may be formed integrally with each other such that both portions are part of the same sheath. Holes 57 disposed in the fluid-conducting portion 112 just proximally of the distal portion 111 of the sheath communicate with one or more lumens inside the sheath, thereby allowing a surgeon to either introduce or drain fluids from a surgical site. The sheath shown in FIG. 19 has a distal portion 111 with a relatively small radius, since the sheath closely conforms to the arthroscope at the distal portion of the arthroscope. This provides the surgeon with the capability of inserting the arthroscope into narrow surgical sites. In addition, the fluid-conduction portion still allows a surgeon to irrigate the surgical field with the combined sheath/arthroscope instrument.

Figure 20:
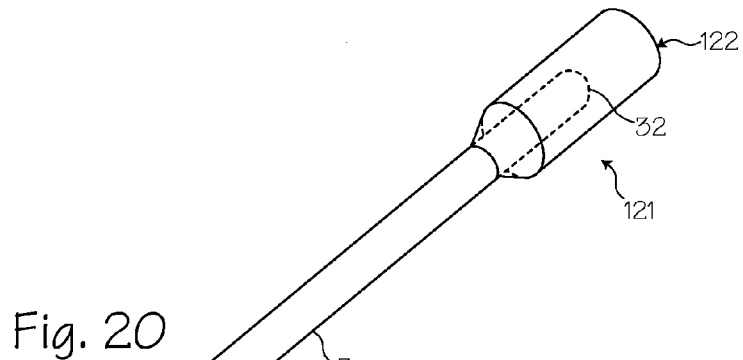
FIG. 20 shows an atraumatic sheath and an elastic grip disposed on the proximal portion of the sheath.
Figure 21:
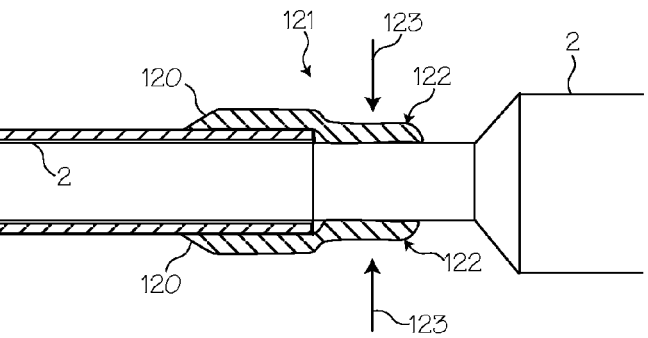
FIG. 21 shows a cross section of an atraumatic sheath disposed over an arthroscope and an elastic grip disposed on the proximal portion of the sheath.

FIGS. 20 and 21 show an atraumatic sheath 3 disposed over an arthroscope 2 and an elastic grip 120 disposed on the proximal portion 121 of the sheath. The grip 120 is preferably a hollow, ergonomic cylinder of elastic material (such as a thermoplastic elastomer) that is sized and dimensioned to allow a surgeon to manipulate the arthroscope and sheath easily, even if the surgeon's hands become wet. The grip extends proximally of the proximal end 32 of the sheath so that the proximal portion 122 of the grip will extend over an arthroscope 2 disposed within the sheath 3. (The proximal portion 121 of the sheath in FIG. 20 is shown in phantom to indicate its position inside the grip.) The grip is designed such that the grip is biased to assume a shape having an inner diameter less than the outer diameter of the arthroscopic instrument and preferably less than the inner diameter of the sheath's inner lumen. Thus, the grip will exert an inwardly directed radial force, as indicated by arrows 123 in FIG. 21, against an instrument disposed within the sheath.

In use, the proximal portion 122 of the grip 120 will squeeze down on and grasp an arthroscope 2 disposed within the sheath 3. If the proximal portion of the grip is peeled back and released, the grip is biased to spring back to its original shape. Thus, the arthroscope will remain secure within the sheath as the arthroscope or sheath is manipulated during surgery.

Figure 22:
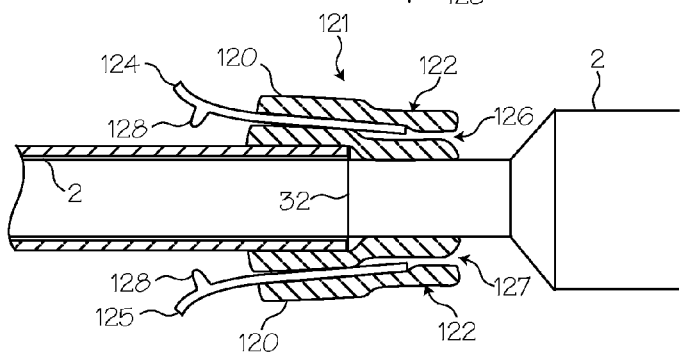
FIG. 22 shows a cross section of an atraumatic sheath disposed over an arthroscope, an elastic grip and levers disposed inside the grip.

FIG. 22 shows a cross section of an atraumatic sheath 3 disposed over an arthroscope 2, an elastic grip 120 and levers 124 and 125 disposed inside the grip for widening the proximal opening of the grip. The grip shown in FIG. 22 is provided with a first channel 126 and a second channel 127 into which a corresponding first lever 124 and second lever 125 have been inserted. The levers are provided with barbs, tangs or other means for securing the levers within their respective channels. The distal portions of the levers are provided with an arcuate shape such that the levers bend away from the sheath.

In use, a user presses on the distal portions of the levers. As the distal portions of the levers move radially inwardly, the proximal portions of the levers will exert a force directed radially outwardly against a corresponding segment of the proximal portion of the grip, thereby bending the proximal portion of the grip radially outwardly. This action widens the proximal opening of the grip. With the proximal opening of the grip widened, the user may easily insert or remove the arthroscope from the sheath. Fulcrums 128 disposed on the distal portions of the levers prevent the levers from moving radially inwardly by more than a pre-determined amount. The fulcrums also allow a user to apply more outward force to corresponding segments in the proximal portion of the grip, thereby making the insertion of instruments easier.

Figure 23:
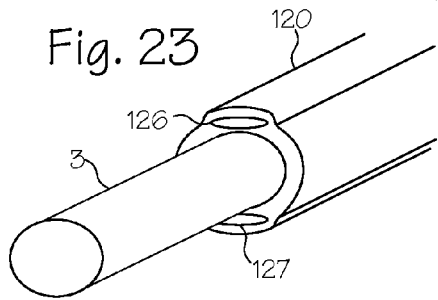
FIG. 23 shows the distal end of the grip.
Figure 24:
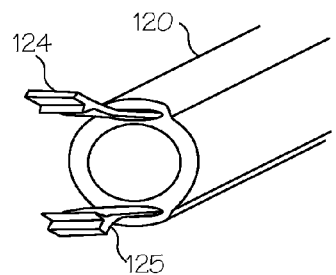
FIG. 24 shows the distal end of the grip and levers extending distally from the openings in the grip.

FIGS. 23 and 24 show the distal end of the grip 120 and levers 124 and 125 extending from the distal end of the grip. A portion of the sheath 3 is shown extending distally from the grip in FIG. 23 for reference. Channels 126 and 127 disposed in the grip extend longitudinally through (or partially through) the grip to accommodate the levers. In use, a user presses on the levers to peel back the proximal portion of the grip. The user then slides the arthroscope into or out of the sheath as desired.

FIG. 25 shows the distal portion of an atraumatic sheath 3 and an arthroscope 2 extending distally of the distal end 140 of the sheath 3. Holes 57 are provided in the distal portion of the sheath. The holes communicate with one or more lumens in the sheath. The lumen or lumens communicate with a vacuum source, fluid source, therapeutic agent source or a combination of sources. Thus, the holes provide for the inflow and outflow of fluids during a procedure.

The distal tip 141 of the sheath is made of an elastic material having a higher modulus of elasticity than the modulus of elasticity found in the material of the proximal portion of the sheath. In another embodiment, the sheath and the distal tip 141 may be manufactured from a single flexible sterilizable polymer. The distal tip of the sheath also has an inner diameter that is slightly smaller than the outer diameter of most arthroscopes. In another embodiment, the sheath and the distal tip 141 may be manufactured from a single flexible sterilizable polymer.

In use, a user inserts the arthroscope into the sheath. The distal tip expands as the distal end of the arthroscope slides past the distal tip of the sheath. Because the inner diameter of the tip is less than the outer diameter of the arthroscope, the tip will form a fluid-proof seal with the arthroscope.

FIG. 26 shows the distal portion of an atraumatic sheath 3 and an arthroscope 2 extending distally of the distal end 140 of the sheath. Holes 57 are provided in the sheath to allow the inflow and outflow of fluids during a surgical procedure. The distal tip 141 of the sheath is made of an elastic material having a hardness that is less than the hardness of the proximal portion of the sheath. A slit 142 is provided in the tip and may extend into the distal portion of the sheath. In use, the slit and tip expand as a user slides an arthroscope through the tip. Thus, the slit allows the sheath to accommodate larger arthroscopes or other medical instruments.

Since the atraumatic sheath may be designed or sized and dimensioned to conform to differently shaped instruments, the sheath is also useful with other medical instruments and other surgical procedures in which it is desirable to protect surrounding tissue from accidental trauma. For example, the atraumatic sheath may be disposed over a trimming instrument for use during arthroscopic surgery or over an energy-delivering medical instrument, such as a laser or RF energy instrument. Other procedures in which the atraumatic sheath is useful include laparoscopic surgery and other kinds of endoscopic surgery. For thin arthroscopes or other fragile medical instruments, the walls of sheath may be provided with braided carbon fibers or a mesh of steel, plastic or other composite that resists bending. As the sheath and instrument bend, force is transferred to the mesh within the sheath, thereby protecting the fragile instrument inside the sheath. In addition, the various sheath configurations shown herein may be combined to form additional types of instrument sheaths. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A method of performing arthroscopic surgery, said method comprising the steps of:
   providing a system for performing arthroscopic surgery, said system comprising:
   an arthroscopic instrument suitable for performing an arthroscopic surgical procedure, said arthroscopic instrument characterized by a proximal end;
   an atraumatic sheath comprising a tube characterized by a proximal portion and a proximal end, said sheath having an outer surface, said sheath having an inner diameter sized and dimensioned to closely conform to an outer diameter of the arthroscopic instrument, wherein the atraumatic sheath is adapted to be removably disposed over the arthroscopic instrument;
   a cylindrical grip disposed coaxially over the outer surface of the sheath on the proximal portion of the sheath, said grip characterized by a proximal portion;
   wherein the proximal portion of the grip extends proximally past the proximal end of the sheath;
   wherein the material of the proximal portion of the grip and the size and dimensions of the proximal portion of the grip are selected such that the proximal portion of the grip is biased to assume a shape having an inner diameter less than the outer diameter of the arthroscopic instrument, whereby the proximal portion of the grip may squeeze the proximal end of the arthroscopic instrument; and
   further comprising a first lever operably attached to the grip, said first lever operable to move a first segment of the proximal portion of the grip in a radially outwardly direction;
   placing the arthroscopic instrument in side the sheath; and
   performing an arthroscopic surgical procedure with the system for performing arthroscopic surgery.

2. The method of claim 1 further comprising a second lever operably attached to the grip, said second lever operable to move a second segment of the proximal portion of the grip in a radially outwardly direction.

3. The method of claim 2 wherein:
   the first lever and the second lever extend distally from the grip;
   the first lever and the second lever are characterized by a distal portion; and
   the distal portions of the first lever and second lever comprise arcuate segments that extend radially outwardly from the sheath.

4. The method of claim 3 further comprising a first fulcrum disposed on the distal portion of the first lever and a second fulcrum disposed on the distal portion of the second lever.

5. The method of claim 1 further comprising a first tab disposed on the sheath, said tab adapted to prevent fluids disposed outside the sheath from moving proximally of the tab.

6. The method of claim 5 further comprising a second tab disposed on the sheath and distally of the first tab, said second tab adapted to prevent fluids disposed outside the sheath from moving proximally of the second tab.

7. The method of claim 5 wherein the sheath is further characterized by a distal portion and wherein the sheath further comprises a hole disposed in the distal portion of the sheath, said hole communicating from the outer diameter of the sheath to a lumen disposed within the sheath, whereby fluids may be introduced into and suctioned from a surgical site through the hole.

8. The method of claim 1 wherein the sheath is characterized by a distal tip and wherein:
   the distal tip comprises a material having a hardness less than the hardness of the material of the sheath; and
   the distal tip has an inner diameter less than the inner diameter of the sheath.

9. The method of claim 8 wherein the tip is split in at least one location on the tip.

10. The method of claim 8 wherein the sheath is further characterized by a distal portion and wherein the sheath further comprises a hole disposed in the distal portion of the sheath, said hole communicating from the outer diameter of the sheath to a lumen disposed within the sheath, whereby fluids may be introduced into and suctioned from a surgical site through the hole.

11. The method of claim 1 wherein the sheath is further characterized by a distal portion and wherein the sheath further comprises a hole disposed in the distal portion of the sheath, said hole communicating from the outer diameter of the sheath to a lumen disposed within the sheath, whereby fluids may be introduced into and suctioned from a surgical site through the hole.

12. A method of performing arthroscopic surgery, said method comprising the steps of:

providing a system for performing arthroscopic surgery, said system comprising:
 an arthroscopic instrument suitable for performing an arthroscopic surgical procedure;
 an atraumatic sheath comprising a tube characterized by a proximal portion and a proximal end, said sheath having an inner diameter sized and dimensioned to closely conform to an outer diameter of the arthroscopic instrument, wherein the atraumatic sheath is adapted to be removably disposed over the arthroscopic instrument;
 a cylindrical grip disposed on the proximal portion of the sheath, said grip characterized by a proximal portion;
 wherein the proximal portion of the grip extends proximally past the proximal end of the sheath;
 wherein the material of the proximal portion of the grip and the size and dimensions of the proximal portion of the grip are selected such that the proximal portion of the grip is biased to assume a shape having an inner diameter less than the outer diameter of the arthroscopic instrument, whereby the proximal portion of the grip may squeeze the arthroscopic instrument;
 a first lever operably attached to the grip, said first lever operable to move a first segment of the proximal portion of the grip in a radially outwardly direction;
 a second lever operably attached to the grip, said second lever operable to move a second segment of the proximal portion of the grip in a radially outwardly direction;
 wherein the first lever and the second lever extend distally from the grip;
 the first lever and the second lever are characterized by a distal portion;
 and the distal portions of the first lever and second lever comprise arcuate segments that extend radially outwardly from the sheath; and
 further comprising a first fulcrum disposed on the distal portion of the first lever and a second fulcrum disposed on the distal portion of the second lever;
placing the arthroscopic instrument in side the sheath; and
performing an arthroscopic surgical procedure with the system for performing arthroscopic surgery.

* * * * *